(12) United States Patent
Youssef

(10) Patent No.: US 6,916,795 B1
(45) Date of Patent: Jul. 12, 2005

(54) ENERGY-PROTECTIVE COMPOSITION COMPRISING ADENOSINE PHOSPHATES

(75) Inventor: Nazih R. Youssef, Wheeling, WV (US)

(73) Assignee: N.R. Youssef, LLC, Wheeling, WV (US)

(*) Notice: Subject to any disclaimer, the term of this patent is extended or adjusted under 35 U.S.C. 154(b) by 0 days.

(21) Appl. No.: 10/459,584

(22) Filed: Jun. 12, 2003

Related U.S. Application Data

(60) Provisional application No. 60/388,377, filed on Jun. 14, 2002, and provisional application No. 60/389,485, filed on Jun. 19, 2002.

(51) Int. Cl.$^7$ .............................................. A61K 31/70

(52) U.S. Cl. ...................... 514/47; 537/26.23; 537/26.7

(58) Field of Search ........................ 514/47; 536/26.26, 536/26.23, 26.7

(56) References Cited

PUBLICATIONS

Tikhomirova et al., "Comparative Radioprotective Effect of Adenylates Against Short–Term and Long–Term γ–Radiation," *Radiobiologiya,* 23(1), 100–104 (Sep.–Oct., 1983); *Chemical Abstracts,* 98, HCAPlus & CA Abstr. No. 157174 (1983); only HCAPlus Abstract supplied; applicant copy; see PTO–1449 AW).*
Grozdov, S. P., "Comparative Study of the Therapeutice Effect of Adenyl Compounds and their effect on Metabolism in Radiation Sickness," *Radiobiologiya,* 20(4), 524–530 (1980); *Chemical Abstracts,* 93, Abstract No. 179729 (HCAPlus No. 579729) (1980).*
Pantev et al., "Antiradiation Mixture and Ionic–bond of AET and Adenyl Nucleotides," *Strahlentherapie und Onkologie,* 167(7), 422–426 (Jul., 1991); *Medline No. 91313485;* only Medline Abstract supplied; applicant copy; see PTO–1449 AT).*
Koshcheenko, N. N., "Biochemical Mechanism of the Radioprotective Action of Adenylic Compounds," *Nauchnye Doklady Vysshei Shkoly Biologicheskie,* (Issue No. 2), pp. 5–18 (1992); *Medline No. 82161127;* only Medline title and citation supplied.*
Ivnitsky et al., "Mechanisms of Cerebral Radiation Syndrome," *Radiatsionnaya Biologiya, Radioekologiya,* 41(1), 48–55 (2001); *Chemical Abstracts,* 135, Abstr. No. 269359 (HCAPlus No. 271063) (2001; only HCAPlus Abstract supplied.*
Nosov et al., "Metabolic Correction of Cerebral Radiation Syndrome," *Radiation Research,* 152(5), 523–529 (1999); *Chemical Abstracts,* 132, Abstr. No. 20542 (HCAPlus No. 714176) (1999).*
Pospilsil et al., "Radioprotection of Mouse Hemopoiesis by Dipyridamole and Adenosine Monophospohate in Fractionated Treatment," *Radiation Research,* 142(1), 16–22 (1995); *Chemical Abstracts,* 122, Abstr. No. 259989 (HCAPlus No. 487342 ) (1999).*

Grozdov et al., "Influence of ADP on the Course of Radiation Sickness and Some Metabolic Processes in Rats After Irradiaiton of the Abdomen and Parenteral Feeding," *Radiobiologiya,* 25(2), 234–238 (1985); *Chemical Abstracts, 103,* Abstr. No. 2971 (HCAPlus No. 402971 ) (1985).*
Savitskii et al., "Liver 5–Nucleotidase Activity of Rats with Radiation Sickness and Under Administration of ATP," *Radiobiologiya,* 20(1), 103–106 (1980); *Chemical Abstracts,* 92, Abstr. No. 193556 (HCAPlus No. 193556) (1980).*
Nikolov et al., "Therapeutic Effect of Adenosine Triphoshate Upon Survival Rate of Irradiated Rats," *Rentgenologiya i Radiologiya,* 8(4), 209–214 (1969); *Chemical Abstracts, 74,* Abstr. No. 72504 (HCAPlus No. 72504) (1971).*
Rogozkin et al., "Adenosine Triphosphoric Acid as Prophylactic and Therapeutic Drug During Radiation Sickness," *Suvremenna Meditsina,* 21(6), 12–18 (1970); *Chemical Abstracts,* 74, Abstr. No. 10149 (HCAPlus No. 10149) (1971); only HCAPlus Abstract supplied.*
Wagner et al., "Chemical Protection Against X–Radiation in the Guinea Pig. I. Radioprotective Action of RNA and ATP," *International Journal of Radiation Biology and Related Studies in Physics, Chemistry and Medicine,* 12(2), 101–112 (1967); *Chemical Abstracts,* 67, Abstr. No. 70960 (HCAPlus No. 470960) (1967); only HCAPlus Abstract supplied.*
Cantley, Jr., et al., "Vanadate Is a Potent (Na,K)–ATPase Inhibitor Found in ATP Derived From Muscle," *Journal of Biological Chemistry,* 252(21), 7421–7423 (Nov. 10, 1977).*
Beaugé et al., "A Modifier of ($Na^+ + K^+$) ATPase in Commercial ATP," *Nature,* 268, 355–356 (Jul. 28, 1977).*
Josephson et al., "Isolation of a Potent (Na–K)ATPase Inhibitor from Striated Muscles," *Biochemistry,* 16(21), 4572–4578 (Oct. 18, 1977).*
Anon, *Sigma Catalog –Biochemicals and Reagents for Life Science Research,* 1997, St, Louis, MO, only pp. 65–66 supplied.*
Lehninger, *Biochemistry, Second Edition,* Worth Publishers, Inc., New York NY, Jul., 1978, only pp. 315–316 supplied.*
Sugahara et al., "Recovery from Radiation Injury with Nucleotide Mixtures in Mice," *Folia Biol. (Prague),* 10(6), 461–464 (1964); *Chemical Abstracts,* 62, Abstr. No. 75954 (HCAPlus No. 75954 ) (1965).*
Senagore et al., "Adenosine Triphosphate–Magnesium Chloride in Radiation Injury," *Surgery,* 112(5), 933–939 (Nov., 1992); Medline No. 93068804.*

(Continued)

Primary Examiner—James O. Wilson
Assistant Examiner—L. E. Crane
(74) Attorney, Agent, or Firm—Hoffman, Wasson & Gitler

(57) ABSTRACT

Compositions comprising the nucleotides adenosine diphosphate and adenosine monophosphate, and their use for neutralizing effects of excess incident energy on the human body, particularly effects of ionizing radiation from nuclear or radiological energy sources, are disclosed and claimed.

12 Claims, No Drawings

PUBLICATIONS

Szeinfeld et al., "Response of Normal BALB/c Mouse Tissue to p(66 MeV)/Be Fast Neutron Radiation: Protection by Exogenous ATP," *Strahlentherapie und Onkologie, 168*(3), 174–178 (Mar., 1992); *Medline Accession No. 92205514.**

A. L. Lehninger, *Biochemistry, Second Edition*, Worth Publisher, Inc., New York, NY, Jul., 1978, only pp. 315, 316 and 400 supplied..*

Sigma Chemical Co., *Biochemicals—Organic Compounds—Diagnostic Reagents (1995 Catalog)*, St. Louis, MO, 1995, only pp. 45–46 supplied.*

J. F. Weiss††, "Pharmacologic Approaches to Protection Against Radiation–induced Lethality and Other Damage," *Environmental Health Perspectives, 105*(Suppl. 6), 1473–1478 (Dec., 1997).*

Venes et al. (eds.), *Taber's Cyclopedic Medical Dictionary, 19th Edition*, F. A. Davis Co., Philadelphia, PA, 2001, only pp. 1817–1818 supplied.*

Sugahara et al., "Recovery from Radiation Injury with Nucleotide Mixtures in Mice," *Folia Biol. (Prague), 10*(6), 461–464 (1964); *Chemical Abstracts, 62*, Abstr. No. 75954 (HCAPlus No. 75954 ) (1965); only HCAPlus Abstract supplied.*

Kozyreva EV; Eliseenko NN; Iashkin PN; Tikhomirova MV; "Radiobiologiia," 1977 Sep.–Oct.; 17(5):733–8.

Tikhomirova MV; Rogozkim VD; "Radiobiologiia," 1979 Mar.–Apr.; 19(2):241–5.

Pantev T; Georgieva R; Topalova S; "Strahlentherapie und Onkologie:Organ der Deutschen Rontgengesellschaft . . . " 1991 Jul.; 167(7):422–6.

Grant GA; Barlow JA; Leach KE; "Strahlentherapie," 1976, 152(3):285–91.

Langendorff H; Langendorff M; "International Journal of Radiation Biology and Related Studies in Physics, Chemistry, and Medicine," 1971; 19(5):493–5.

Tikhomirova MV; Iashkin PN; "Radiobiologiia," Jan.–Feb. 1983; 23(1):100–4.

Langendorff H; Langendorff M; "Strahlentherapie," 1972, 144(4):451–6 (Oct., 1972).

Langendorff H; "Die Naturwissenschaften," 1970, 57(9);455 (Sep., 1970).

* cited by examiner

ENERGY-PROTECTIVE COMPOSITION COMPRISING ADENOSINE PHOSPHATES

The instant application is based upon U.S. provisional patent application Ser. No. 60/388,377, filed Jun. 14, 2002 and U.S. provisional patent application Ser. No. 60/389,485, filed Jun. 19, 2002, the disclosures of which are included herein by reference.

BACKGROUND OF THE INVENTION

1. Field of the Invention

The invention relates to compositions for protecting biological systems against excessive amounts of ambient energy, particularly electromagnetic energy. In particular, the invention relates to energy-protective compositions comprising the di- and monophosphates of the nucleoside adenosine.

The primary source of the energy required for life on this planet is our sun, whose radiations are propagated through space as waves of electromagnetic energy in a continuous spectrum of wavelengths ranging from less than 1 nm to more than 3 mm. Ionizing radiations (those capable of displacing an electron from an atom) are somewhat arbitrarily considered to be those having wavelengths less than about 1 nm and photon energies of more than 1 keV, while radiations having longer wavelengths and less energy are considered to be non-ionizing radiation. While most solar high-energy radiation is scattered or reflected in the upper atmosphere (e.g., gamma- and x-rays) or absorbed in the ozone layer (e.g., far ultraviolet (UV-C) rays), most non-ionizing radiation comprising near-UV (UV-A) and mid-UV (UV-B), visible light (VIS), and infrared (IR), readily reaches the earth's surface.

In addition to this solar radiation, background electromagnetic radiation from other natural and artificial sources is present. Particularly significant non-ionizing radiation includes IR (heat) waves from all high temperature heat sources and radiofrequent (RF) waves from radio and television broadcast stations, portable phones, radar installations, microwave equipment, and interstellar space. Common non-solar sources of ionizing background radiation include cosmic rays, radioactive isotopes endogenous to the earth and its surroundings, continuing fallout from past nuclear weapons tests, emissions from nuclear energy sites, radioactive waste, and radioisotopes and radiological and laser equipment used in medical and other scientific procedures and research.

Although biological systems are dependent upon solar radiation, it is a double-edged sword since excess exposure can overwhelm an organism's protective and repair mechanisms and cause potentially irreparable damage. UV, VIS, and IR radiation do not deeply penetrate the body; the energy is absorbed by the skin and/or eyes and converted to thermal (heat) energy which is dispersed throughout the system and ultimately captured and stored for future use in the form of adenosine triphosphate (ATP), the universal energy carrier. Under normal circumstances, absorption and conversion of this energy merely creates a harmless local thermal effect; if, however, the rate of energy incidence exceeds the rate of energy dispersion (as when the subject is too close to the source of energy or exposed too long or too often), energy states at the absorption site will increase to higher levels owing to accumulation of energy, with concomitant increase in the potential for macroscopic (tissue) and microscopic (cellular and biomolecular) damage.

Of particular concern is electromagnetic radiation which deeply penetrates the body, as even small doses will scatter through the tissues and rapidly overwhelm natural defense and repair mechanisms, leading to widespread submicroscopic damage. Radiations with these penetrating capabilities are primarily short wavelength/high frequency ionizing radiations from both artificial and natural sources (supra), but some RF radiation also has penetrating capabilities. Absorption of such radiation above a very low threshold can have substantial adverse biological effects, including neoplastic transformation of cells and other cell mutations owing to irreparable DNA damage.

As the biological response to absorbed electromagnetic energy is normally dependent upon the quantity of absorbed energy rather than its position on the electromagnetic spectrum, protection from repeated exposure to relatively low-energy or non-ionizing radiation such as near UV radiation can be as necessary as protection from intermittent exposure to high-energy or ionizing radiation such as x-rays and gamma rays. In either case, given an energy incidence of sufficient magnitude over sufficient time, covalent bonds which determine the structure and properties of biomolecules throughout the system are disrupted. If the repair system cannot cope with this disruption, permanent damage to DNA and other critical macromolecules will result, with serious health consequences to the individual and potentially to the species.

The tolerance of the human body for electromagnetic radiation is not certain, particularly since the effects of the energy are cumulative; tolerance varies with age; and the damage, especially genetic damage, may not manifest itself for many years, perhaps generations. It is known that the effects of ordinary ambient electromagnetic radiation can be reduced by the practice of avoiding sources or shielding the body with common materials to reduce exposure. However, the general population has no effective means for defending itself against a sudden devastating release of high energy radiation from nuclear or other sources. It is thus imperative to provide alternate methods and means for safely and effectively minimizing the biological effects of whole-body radiation exposure, both ordinary and catastrophic, to the extent possible. Since a significant cause of radiation damage is the energy load absorbed by the body from the radiation passing through it, neutralizing this energy at the biomolecular level is a viable approach.

2. Discussion of Related Art

It has previously been proposed to enhance the energy conversion and/or storage capabilities of human or other animal bodies by the administration of compounds or compositions theoretically capable of capturing and/or storing absorbed energy which threatens biological protection and repair mechanisms. Of some interest has been ongoing research in the former Soviet Union and elsewhere on compositions comprising one or more adenyl nucleotides (adenosine phosphates), often in combination with one or more other proposed energy receptors.

For example, adenosine diphosphate (ADP) has been described as having a protective action in experimental animals when administered prior to and after gamma irradiation [*Radiobiologiia*, 1977, 17(5):733–8; *Radiobiologiia*, 1979, 19(2):241–5; *Radiobiologiia*, 1983, 23(1):100–4]. Similar activity has been reported for ATP, AMP (3'-monophosphate and 5'-monophosphate), and cAMP (cyclic adenosine monophosphate, 3',5'-monophosphate), alone or in combination with each other [*Strahlentherapie*, 1976, 152(3):285–91; *Int J Radiat Biol Relat Stud Phys Chem Med*, 1971, 19(5):493–5; *Radiobiologiia*, 1983, op. cit.; *Strahlentherapie*, 1972, 144(4):451–6; and *Die Naturwis-*

*senschaften* 1970, 57(9):455]. Additionally, adenosine triphosphate and its mono- and diesters have been combined in various ways with AET (2-aminoethylisothiuronium halide) for radiation protection [*Strahlenther Onkol,* 1991 July; 167(7):422–6]. While such studies have generally reported some increased resistance to irradiation in the animals treated with these compounds or compositions compared to untreated controls, the effectiveness of the treatments over time (long-term survival rates) has only marginally improved.

SUMMARY OF DISCLOSURE

Compositions and methods for protecting the human body from excess incident energy, particularly electromagnetic energy, comprise compositions of adenosine diphosphate (ADP) and adenosine monophosphate (AMP) administered by any convenient route. Protection from ionizing radiation, especially γ-rays, x-rays, and β-particles is emphasized.

DETAILED DESCRIPTION OF THE INVENTION

The invention provides adenosine diphosphate/adenosine monophosphate energy-protective compositions which minimize the effects of excessive energy exposure across a complete continuous electromagnetic spectrum as set forth in the following Table (wavelengths and energies may vary slightly with the data source):

| Type | Wavelength | Photon Energy (in eV) |
|---|---|---|
| Ionizing | less than 1 nm | more than 1 keV |
| Far-UV (UV-C) | 1–280 nm | ⎫ |
| Mid-UV (UV-B) | 280–315 nm | ⎬ 0.3–1 keV |
| Near-UV (UV-A) | 315–400 nm | ⎭ |
| Visible (VIS) | 400–780 nm | 0.15–0.3 eV |
| Near-IR (IR-A) | 780–1400 nm | ⎫ |
| Mid-IR (IR-B) | 1400–3000 nm | ⎬ 0.15–40 meV |
| Far-IR (IR-C) | 3000 nm–3 mm | ⎭ |
| Radiofrequent (RF) | >3 mm | less than 40 meV |

Adenosine triphosphate (ATP) is a nucleotide endogenous to all animals, responsible for transporting energy throughout the body to meet cell requirements. It is a high energy molecular structure poised for release of bioenergy through hydrolysis of its phosphoanydride bonds as shown in the following half-reactions:

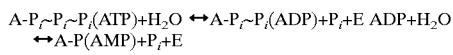

$$A\text{-}P_i\text{~}P_i\text{~}P_i(ATP)+H_2O \leftrightarrow A\text{-}P_i\text{~}P_i(ADP)+P_i+E \; ADP+H_2O$$
$$\leftrightarrow A\text{-}P(AMP)+P_i+E$$

wherein:
~is a phosphoanhydride bond;
- is a phosphoester bond;
A is adenosine;
$P_i$ is inorganic phosphate; and
E is bioenergy.

As indicated, the half-reactions are each reversible, representing the synthesis of ATP from ADP and AMP, given the presence of ATP synthase (ATPase), a store of available inorganic phosphate, and the energy normally supplied to the body by food and sunlight. The mechanisms by which these reactions proceed in vivo have been thoroughly elaborated (e.g., Walker and Boyer, Nobel Prize for Chemistry, 1997). The present invention exploits these endogenous cellular mechanisms by creating an environment comprising supplementary ADP and AMP, which promotes ATP synthesis with the depletion of absorbed radiation energy as described in further detail below.

According to the inventions, the energy-protective composition provides a reservoir of primary molecules (ADP and AMP) capable of neutralizing an abnormally high energy load through conversion of these components to their higher phosphates with an uptake of this absorbed energy. Excessive incident energy (that which exceeds the body's normal energy dispersion/storage capabilities) is absorbed and converted by the body to free bioenergy which drives phosphorylation of the mono- and di-adenosine phosphates of the invention, effectively neutralizing this excess energy by formation of the phosphoanhydride bonds. The body is thus enabled to spare itself adverse effects of excessive radiation exposure by drawing on this reservoir for ATP synthesis with transduction of excess incident energy.

The invention is also predicated on the concept that the energy-requiring step of ATP synthesis is the formation of an enzyme/phosphate/ester complex preparatory to the phosphorylation of AMP or ADP, while decomposition of ATP with the production of energy is effected by a different mechanism. The compositions of the invention thus contain two active components for synthesizing ATP and consequently sequestering absorbed energy, in marked contrast to prior art compositions based on ATP alone or ATP in combination with one or more lower esters. Thus, the combination of active components as described herein obtains its results at least in part by successfully enhancing the energy storage capabilities of the body.

The essential components of the composition, AMP and ADP, are widely commercially available. As indicated above, each of these compounds comprises an adenine-ribose (nucleoside) structure wherein one of the 3 free ribose hydroxyl groups has been phosphoesterified to form the corresponding nucleotide; in the case of ADP, this phosphoester group has been further phosphorylated to form the diphosphate species. These hydroxyl groups are located at the 2',3', and 5' carbon atoms of ribose, and phosphorylation at any one of these sites yields the corresponding 2', 3', or 5' monophosphate or diphosphate. Any one of these species as well as 3',5'-AMP (cylic AMP, cAMP) is contemplated to be useful in the practice of the inventions. As phosphorylation at the 5° C. hydroxyl group appears to occur preferentially in nature (this hydroxyl group is part of an alcohol group), it may be more advantageous to use compositions containing 5'-ADP and/or 5'-AMP, rather than the 3' or 2' or 3',5' species. Accordingly, the terms "AMP" and "ADP" as used herein broadly encompass each of 2'-, 3'-, and 5'-AMP and ADP, respectively, and 3'5'-cAMP, except as otherwise noted. The composition can further contain inorganic phosphate, in the form of any of its convenient physiologically-compatible salts, such as calcium or magnesium phosphate; in appropriate molar ratios to the ADP/AMP components.

In an exemplary embodiment, the composition of the invention comprises from about 60–98% by wt. ADP and about 2–40% by wt. AMP, based on the combined weight of ADP and AMP in the composition; preferably, the composition comprises from about 80 to 98% ADP and from about 2 to 20% AMP, or from about 90 to 95% ADP and from about 5 to 10% AMP. The active nucleotide ingredients should preferably be food grade or better for oral administration and pharmaceutical grade for most parenteral administrations. The composition may contain customary excipients in addition to the active ingredients; however, the amount of combined active ingredients should not be diluted by more than about an equal amount of inert additives for best results. The composition may be administered orally in relatively small individual doses, for example, as a nutritional supplement for long-term protection against the cumulative effects of normal foreground and background radiation; topically as, for example, a sunscreen ointment or lotion; or intravenously, subcutaneously, or intramuscularly, as well as orally, in relatively high doses in situations requiring immediate protection against high-energy radiation. Slow-release forms of the dosage, such as skin patches, are also contemplated for use in connection with ongoing exposure. For typical use, the active components are admixed with at least one suitable inert vehicle as known in the art, such as physiological saline or distilled water for injectible formulations; sugar or starch fillers for solid oral dosage forms; or oil-based creams for topical ointment or lotion preparations.

The compositions of the invention are used either prophylactically (in advance of exposure) or therapeutically (post-exposure) or both. Ideally, the compositions should be administered at least prior to exposure if possible. As the active components of the compositions decay relatively rapidly in the body (losing about 50% of activity in about 20 minutes), they should be administered as near to exposure as possible, preferably within about a half-hour of exposure if at all practicable. For example, for protection against a sudden substantial dosage of ionizing radiation such as might be encountered upon detonation of a nearby nuclear device or failure of a nuclear energy plant, it is greatly preferred that high i.v. or i.m. dosages be administered within at least about a half-hour prior to exposure, and within a half-hour after exposure. For intermittent, smaller ionizing radiation dosages such as might be encountered clinically, relatively high oral dosages may be sufficient. Follow-up administration, for example, in daily doses, is also recommended for at least several days after exposure to excessive radiation, especially to high-energy radiation, since the systemic effects of radiation continue for a long time and the effects are cumulative.

In practice, compositions according to the invention are administered in amounts of from about 0.8 to about 18 mg/kg body weight, depending upon the potency of the radiation dosage. Composition dosages at the higher end of the dosage range will typically be given, for example, in emergency situations involving high radiation dosages of ionizing radiation, preferably intravenously or intramuscularly in single or multiple individual doses, or a continuous drip. In non-life-threatening situations, the compositions may be administered in doses at the lower end of this range by other more convenient routes (such as topically or orally) over periods of time coinciding with exposure.

The invention further includes methods for protecting biological systems from the effects of excessive incident energy using the compositions of the invention. The methods of the invention include the prophylactic and/or therapeutic use of the compositions on a regular basis for protecting these systems from the cumulative effects of ordinary foreground and background energy. They also include prophylactic and/or therapeutic methods for protecting these systems against energy overloads caused by exposure to relatively high spikes of high energy radiation from, e.g., medical or other scientific equipment or tools such as x-ray or radiation therapy equipment and radiolabelled diagnostic material; occupational radiation hazards such as nuclear power plants, radioactive waste, and nuclear science laboratories; and recreational equipment such as tanning devices and cell phones operating at high frequencies. They are particularly suitable for protection against e.g., clinical x-ray exposures, as the protective effects of the composition are generated at the cellular level and do not affect the atomic number or the atomic weight of the body and consequently do not interfere with the quality of the x-ray films.

Contemplated specific uses for the compositions of the invention include protection against background or foreground ionizing radiation in war or peace; protection against heat (IR radiation), for example, heat buildup under protective clothing, sun strokes, or hyperthermia during anaesthesia; as a potassium iodide substitute which will protect the entire body, not just the thyroid gland, against high-energy radiation including X-rays. Protection against excessive mechanical energy, e.g., potential and kinetic energy such as applied in the course of physical trauma, is also contemplated.

The practice of the inventions is applicable to any biological system utilizing ATP as an energy source via the mechanisms described, particularly animals, including humans. It is contemplated that the compositions of the invention will be effective up to about a 15,000 rad cumulative dosage. At some point above this dosage, the body is subject to severe trauma dispositive of survival, typically progressive damage to the GI tract, lungs, and then the CNS, which cannot be treated or prevented by the present invention.

In sum, the compositions of the invention are useful for whole-body and partial-body protection against waves of energy falling across a continuous electromagnetic spectrum. These waves differ not at all in their constitution (all have electrical, magnetic and particle functions), but only in their power densities, which are directly related to their wavelengths (frequencies), so that the energy of the original radiation is converted to a different, lower energy as a wave lengthens in response to certain conditions. Further, energy supplied to the body and calculated in calories, for example, is biologically interchangeable with energy supplied and calculated in electron volts (eV) in the biological synthesis/decomposition of ATP. Owing to the fundamental sameness of energy absorbed by the body, whether supplied as food or as solar radiation or other energy, and the body's ability to convert this energy to levels which safely satisfy its needs, the present inventions are able to exploit natural physiological processes and offer an effective broad spectrum protection against incident energy.

EXAMPLES

Methods and Materials:

An energy protective composition referred to in the following Examples as "ADP/AMP", comprising 66% by wt. ADP, 5% by wt. AMP, and 29% by wt. isotonic normal saline (0.85% NaCl), was prepared for IM or IV administration in the amount of from about 0.8 to about 18 mg/kg of subject. In the following examples, 12 mg/kg of this composition was administered to the subject animals intravenously. This particular composition was selected because, inter alia, it is relatively safe in the therapeutic doses used, and it quickly decays at a rate of about 50% per 20 minutes, creating a favorable sensitization period: long enough to administer the radiation, and short enough to avoid significant complications.

EXAMPLE I:

Animal Tolerance Assessment with Tumor Evaluation

Erlich ascitic tumors were implanted in the left flank of each of 19 1–3 CF-1 mice 1–3 months old in three separate subcutaneous sites by injecting a cell-containing fluid. The mice were numbered with ear punches at this time.

The tumors were sufficiently well developed after eight days and at this time the tumor dimensions were recorded.

Five of the mice were taken as controls $C_{0-4}$; $C_0$ died while under ether and the remaining mice survived with comparable tumor implantation. The remaining 14 mice were divided into two experimental groups of seven each according to comparable tumor development (number and size).

Tumor pairs were to be treated with one of three dose levels of radiation (500, 1000 and 2000 rads). Since tumors did not always develop at all three injection sites, it was not possible to treat each mouse with the three dose levels of radiation. The seven mice of Group A received, intravenously, 12 mg/kgm body weight of "ADP/AMP" composition, within 30 minutes before irradiation. The second group (Group B) received no composition. A 2 cm cone was selected so that the exposure area was large enough to include all tumors on each of the mice. An area including the three tumor sites was totally irradiated with 500 rads of radiation by 120 keV X-ray machine. The 500 rad tumor was then shielded, and another 500 rads was administered to the remaining area. Then both of the preceding tumors were lead-shielded while the final 1000 rads was administered. Tumor sites were labeled as T-1, T-2 or T-3.

Tumor measurements were taken and recorded at various intervals. All measurements were taken with a Vernier caliper and diameters noted to the nearest tenth of a millimeter. The experiment was terminated on Day 28.

Results:

The results are tabulated in Chart I. Tumor response as a criterion of tumor lethal dose "T" is not discussed.

Discussion of Animal Survival, "L": Survival of 28 days or more.

For the four control animals without "ADP/AMP" or radiation (Group C): All survived ($C_{1, 2, 3, 4}$).

For the seven animals irradiated (2000 rad maximum) without "ADP/AMP" (Group B): Five died ($B_{1, 2, 3, 5, 6}$).

For the six animals with irradiation (2000 rad maximum) following "ADP/AMP" (Group A): Only one died ($A_3$).

| | |
|---|---|
| A0 died under anesthesia (excluded) | B1 died 6/21 with anal bleeding |
| A1 survived no anal bleeding | B2 died 6/27 with anal bleeding |
| A2 survived no anal bleeding | B3 died 6/24 with anal bleeding |
| A3 died 6/24 no anal bleeding | B5 died 6/24 with anal bleeding |
| A5 survived no anal bleeding | B6 died 6/22 with anal bleeding |
| A6 survived no anal bleeding | B7 survived no anal bleeding |

| Group A (2000 rads) | Group B (2000 rads) |
|---|---|
| *Survival = 4/5 = 80% | Survival 1/6 = 17% |
| *GI protection = 5/5 = 100% | GI protection 1/6 = 17% |
| Group A (500 rad) | Group B (500 rad) |
| — | B4 (1 of 1) survived no anal bleeding |
| Group A (1000 rad) | Group B (1000 rad) |
| A4 (1 of 1) survived no anal bleeding | — |

CHART I

Group A - "ADP/AMP" ("ADP" in chart) plus radiation
Group B - Radiation only
Group C - Control (no radiation, no "ADP/AMP")

| GROUP | TREATMENT | TUMOR SITE | # RADS JUNE 19 | JUNE 18 | JUNE 23 | JUNE 26 | JULY 2 | JULY 7 | JULY 11 | JULY 17 |
|---|---|---|---|---|---|---|---|---|---|---|
| $A_0$ | ADP plus radiation | T-1 | 2000 | 8.0 | 6.0 | Died June 23 from an overdose of ether | | | | |
| | | T-2 | 1000 | 7.4 | 7.8 | | | | | |
| | | T-3 | 500 | 9.0 | 9.0 | | | | | |
| $C_0$ | No ADP nor radiation "Control" | T-1 | — | — | — | Died June 23 from an overdose of ether | | | | |
| | | T-2 | — | — | — | | | | | |
| | | T-3 | — | 5.0 | 7.6 | | | | | |
| $B_1$ | Radiation only | T-1 | 2000 | 4.4 | Died June 21, anal bleeding was apparent at the time of death | | | | | |
| | | T-2 | 500 | 4.2 | | | | | | |
| | | T-3 | 1000 | 6.5 | | | | | | |
| $B_2$ | Radiation only | T-1 | — | — | — | — | Died June 27, anal bleeding was apparent at death | | | |
| | | T-2 | 2000 | 6.0 | 6.2 | 4.9 | | | | |
| | | T-3 | 1000 | 7.3 | 7.0 | 5.9 | | | | |
| $A_3$ | ADP plus radiation | T-1 | 2000 | 7.6 | 7.4 | 7.8 | 5.9 | 0 | 0 | 0 |
| | | T-2 | 500 | 6.3 | 5.1 | 5.4 | 5.0 | 4.8 | 4.4 | 5.9 |
| | | T-3 | 1000 | 7.8 | 7.8 | 7.8 | 5.9 | 5.2 | 3.4 | 0 |
| $A_2$ | ADP plus radiation | T-1 | 1000 | 6.3 | 6.8 | 2.8 | 0 | 0 | 0 | 0 |
| | | T-2 | 2000 | 8.8 | 9.0 | 5.4 | 0 | 0 | 0 | 0 |
| | | T-3 | 500 | 6.9 | 6.9 | 7.4 | 3.8 | 0 | 0 | 0 |
| $B_3$ | Radiation only | T-1 | 500 | 8.5 | 7.2 | Died June 24, anal bleeding was apparent at death | | | | |
| | | T-2 | 1000 | 7.9 | 6.9 | | | | | |
| | | T-3 | 2000 | 8.0 | 7.9 | | | | | |
| $C_1$ | No ADP nor radiation "Control" | T-1 | — | — | — | — | — | — | — | — |
| | | T-2 | — | 5.7 | 9.0 | 11.0 | 11.6 | 12.4 | 14.0 | 14.6 |
| | | T-3 | — | — | — | — | 3.4 | 6.3 | 8.5 | 21.1 |
| $B_4$ | Radiation only | T-1 | — | — | — | — | — | — | — | — |
| | | T-2 | 500 | 10.5 | 9.5 | 6.5 | 5.7 | 0 | 0 | 0 |
| | | T-3 | — | — | — | — | — | — | — | — |
| $B_5$ | Radiation only | T-1 | — | — | — | Died June 24, also anal bleeding | | | | |
| | | T-2 | 2000 | 7.9 | 6.3 | | | | | |
| | | T-3 | 500 | 10.6 | 9.3 | | | | | |

CHART I-continued

Group A - "ADP/AMP" ("ADP" in chart) plus radiation
Group B - Radiation only
Group C - Control (no radiation, no "ADP/AMP")

| GROUP | TREATMENT | TUMOR SITE | # RADS JUNE 19 | JUNE 18 | JUNE 23 | JUNE 26 | JULY 2 | JULY 7 | JULY 11 | JULY 17 |
|---|---|---|---|---|---|---|---|---|---|---|
| $C_2$ | No ADP nor | T-1 | — | — | — | — | 10.7 | 7.2 | 8.6 | 9.0 |
|  | radiation | T-2 | — | 3.9 | 5.7 | 5.0 | 7.7 | 7.7 | 10.2 | 13.4 |
|  | "Control" | T-3 | — | 8.3 | 8.9 | 11.6 | 12.0 | 14.6 | 14.7 | 16.8 |
| $A_3$ | ADP plus | T-1 | — | — | — |  | Died June 24 |  |  |  |
|  | radiation | T-2 | 1000 | 5.2 | 5.2 |  |  |  |  |  |
|  |  | T-3 | 2000 | 6.8 | 6.1 |  |  |  |  |  |
| $C_3$ | No ADP nor | T-1 | — | — | — | — | 4.0 | 10.9 | 12.0 |  |
|  | radiation | T-2 | — | 8.8 | 9.3 | 7.7 | 5.6 | 10.7 | 10.9 |  |
|  | "Control" | T-3 | — | 4.1 | 7.5 | 3.9 | 10.9 | 9.8 | 11.6 |  |
| $C_4$ | No ADP nor | T-1 | — | — | — | — | 5.0 | 9.6 | 10.5 | 14.6 |
|  | radiation | T-2 | — | — | — | — | 4.3 | 6.4 | 12.4 | 15.2 |
|  | "Control" | T-3 | — | 11.3 | 11.6 | 11.9 | 11.0 | 10.6 | 11.6 | 14.7 |
| $A_4$ | ADP plus | T-1 | — | — | — | — | — | — | — | — |
|  | radiation | T-2 | 1000 | 6.5 | 5.2 | 4.9 | 3.6 | 2.3 | 0 | 0 |
|  |  | T-3 | 500 | 9.9 | 10.4 | 10.8 | 5.7 | 5.2 | 0 | 0 |
| $A_5$ | ADP plus | T-1 | 500 | 3.9 | 3.8 | 3.5 | 0 | 0 | 0 | 0 |
|  | radiation | T-2 | 2000 | 7.9 | 7.7 | 5.9 | 5.8 | 4.9 | 0 | 0 |
|  |  | T-3 | 1000 | 5.1 | 4.4 | 6.8 | 4.4 | 0 | 0 | 0 |
| $B_0$ | Radiation only | T-1 | 2000 | 6.6 | Died June 22, and anal bleeding was present at death |  |  |  |  |  |
|  |  | T-2 | 500 | 9.0 |  |  |  |  |  |  |
|  |  | T-3 | 1000 | 5.6 |  |  |  |  |  |  |
| $B_7$ | Radiation only | T-1 | 1000 | 5.3 | 4.0 | 3.4 | 0 | 0 | 0 | 0 |
|  |  | T-2 | 2000 | 7.9 | 5.7 | 4.4 | 2.6 | 2.0 | 0 | 0 |
|  |  | T-3 | 500 | 6.2 | 5.7 | 4.0 | 2.6 | 2.6 | 0 | 0 |
| $A_6$ | ADP plus | T-1 | — | — | — | — | — | — | — | — |
|  | radiation | T-2 | 2000 | 5.9 | 7.3 | 5.0 | 4.2 | 0 | 0 | 0 |
|  |  | T-3 | 500 | 10.2 | 10.6 | 7.3 | 2.5 | 0 | 0 | 0 |

EXAMPLE II:
Animal or Tissue Tolerance Assessment of Animal Protection

Eight CF-1 mice 1–3 months old were given "ADP/AMP" composition intravenously followed by whole body irradiation within 30 minutes. 1100 rads maximum and about 1050 rads minimum were administered with a deep x-ray machine (300 kV, 4 mm Cu HVL). These mice were followed for 30 days.

No controls were used and the results were assessed against previously established results wherein the $LD_{50}$ was reached in 85 hours (i.e., in the present experiment, four mice should be dead then, and all mice should be dead in 30 days).

Results:

| *Survival Time | Established Survival | Example II |
|---|---|---|
| 3½ Days | 4 (50%) | 8 (100%) no anal bleeding |
| 30 Days | 0 (0%) | 1 (10%) no anal bleeding |

Summary of Example II Survival Time

All mice survived for six days (144 hours).
Six mice survived for seven days.
Five mice survived for nine days.
Three mice survived for ten days.
Two mice survived for 25 days.
One mouse (12.5%) survived more than 30 days.

The results demonstrate a dramatic increase in time before the $LD_{50}$ of the exposed population is reached in Example II, in contrast to the established $LD_{50}$. The established survival time of 50% of the population (four mice) is 3.5 days; however, under the experimental conditions here, 100% of the population (eight mice) were alive after 3.5 days; $LD_{50}$ occurred on day 10. This represents a 300% increase in survival time under 1000+ rad.

No anal bleeding was noticed in any of the mice. The mice evidenced a real protection against radiation owing to the presence of "ADP/AMP" composition in their bodies during irradiation. Similar protection of humans against ionizing radiation is expected.

*A significant protection against ionizing radiation was shown by:
  Survival of 80% against only 17% (470% increase) (EXAMPLE I);
  Anal bleeding 0% against 100% (EXAMPLE I); and
  Survival of 100% against 50% at 3½ days and 10% against 0% at 30 days (EXAMPLE II).

What is claimed is:

1. A method for reducing adverse effects of excess incident energy from electromagnetic radiation in the ultraviolet and shorter wavelength portion of the spectrum on a mammalian host in need thereof, comprising administering to the host a composition consisting essentially of adenosine diphosphate (ADP), adenosine monophosphate (AMP), and a pharmaceutically-acceptable carrier; with the proviso that the adenosine nucleotide components of the composition consist of adenosine-5'-diphosphate and adenosine monophosphate selected from the group consisting of adenosine-2'-monophosphate, adenosine-3'-monophosphate, and adenosine-5'-monophosphate.

2. The method of claim 1, wherein the composition consists essentially of from about 60% to 98% by weight ADP and from about 2% to 40% by weight AMP, based on the combined weights of ADP and AMP.

3. The method of claim 1, wherein the composition consists essentially of from about 80% to 98% by weight ADP and from about 2% to 20% by weight AMP, based on the combined weights of ADP and AMP.

4. The method of claim 1, wherein the composition consists essentially of from about 90% to 95% by weight ADP and from about 5% to 10% by weight AMP, based on the combined weights of ADP and AMP.

5. The method of claim 1, wherein the carrier is a liquid carrier for intravenous, intramuscular, or subcutaneous administration.

6. The method of claim 2, wherein the carrier is a liquid carrier for intravenous, intramuscular, or subcutaneous administration.

7. The method of claim 1, wherein the carrier is a solid carrier for oral administration.

8. The method of claim 2, wherein the carrier is a solid carrier for oral administration.

9. The method of claim 1, wherein the carrier is an oil-based carrier for topical administration.

10. The method of claim 2, wherein the carrier is an oil-based carrier for topical administration.

11. The method of claim 1, wherein the excess incident energy is from ionizing radiation.

12. The method of claim 2, wherein the excess incident energy is from ionizing radiation.

\* \* \* \* \*